(12) United States Patent
Henderson et al.

(10) Patent No.: US 7,041,087 B2
(45) Date of Patent: May 9, 2006

(54) PRE-FILLED SYRINGE

(75) Inventors: Malcolm John Henderson, Macclesfield (GB); Toshikazu Hirayama, Osaka (JP); Masafumi Aramata, Osaka (JP)

(73) Assignee: Astrazeneca UK Limited, London (GB)

( * ) Notice: Subject to any disclaimer, the term of this patent is extended or adjusted under 35 U.S.C. 154(b) by 619 days.

(21) Appl. No.: 10/240,002

(22) PCT Filed: Mar. 28, 2001

(86) PCT No.: PCT/GB01/01433

§ 371 (c)(1),
(2), (4) Date: Feb. 5, 2003

(87) PCT Pub. No.: WO01/74424

PCT Pub. Date: Oct. 11, 2001

(65) Prior Publication Data

US 2004/0087906 A1 May 6, 2004

(30) Foreign Application Priority Data

Apr. 3, 2000 (JP) .............................. 2000-105386

(51) Int. Cl.
*A61M 5/28* (2006.01)

(52) U.S. Cl. ...................................... 604/200; 604/415
(58) Field of Classification Search ................ 604/232, 604/199–202, 205, 206, 415
See application file for complete search history.

(56) References Cited

U.S. PATENT DOCUMENTS

| 2,388,634 | A | * | 11/1945 | De Woody | 604/415 |
| 2,659,370 | A | * | 11/1953 | Smith | 604/416 |
| 2,677,374 | A | * | 5/1954 | Burnside | 604/199 |
| 3,989,044 | A | * | 11/1976 | Meierhoefer | 604/192 |
| 4,253,459 | A | * | 3/1981 | Willis | 604/414 |
| 4,781,701 | A | * | 11/1988 | Geprags | 604/240 |
| 5,135,496 | A | | 8/1992 | Vetter et al. | |
| 5,320,603 | A | | 6/1994 | Vetter et al. | |
| 5,501,676 | A | * | 3/1996 | Niedospial et al. | 604/534 |
| 5,624,405 | A | | 4/1997 | Futagawa et al. | |
| 5,785,691 | A | | 7/1998 | Vetter et al. | |
| 5,807,345 | A | | 9/1998 | Grabenkort | |
| 5,833,653 | A | | 11/1998 | Vetter et al. | |
| 6,068,614 | A | * | 5/2000 | Kimber et al. | 604/200 |

* cited by examiner

*Primary Examiner*—Sharon Kennedy
(74) *Attorney, Agent, or Firm*—White & Case LLP

(57) ABSTRACT

A pre-filled syringe comprising a glass barrel (1), a sealing member (5) fitted in a medical liquid discharge port (11) of the barrel (1), a tip member (2) mounted around the sealing member (5) on the medical liquid discharge port (11) of the barrel (1), a closing member (4), a cap member (3), and a holding member (6); the sealing member (5) having a through-hole (51) formed in the axial direction; the tip member (2) including a skirt (24) provided with an engagement pawl (25) on the inner wall of a lower end thereof, a top wall (23), a needle mounting portion (21), and a medical liquid deriving portion (22), and being provided with a medical liquid passage (28); the closing member (4) being inserted into the medical liquid passage (28) and the through-hole (51) to close the through-hole (51) and so prevent oxygen contamination and deterioration of the medical liquid.

14 Claims, 16 Drawing Sheets

PRE-FILLED SYRINGE

REFERENCE TO RELATED APPLICATIONS

This application is a 35 U.S.C. 371 National Stage Application of International Patent Application No. PCT/GB01/01433, filed Mar. 28, 2001.

The present invention relates to a syringe which is filled in advance with a liquid to be injected. More particularly, the invention relates to an improvement in a pre-filled syringe which has a barrel of glass and which can select the position and shape of a needle mounting portion arbitrarily.

In the manufacture of the pre-filled syringe of the prior art using a glass barrel, the needle mounting portion is formed into a hollow nozzle converged, as a so-called "luer tip", into a taper shape. This luer tip may be formed by (i) a method of working a glass pipe; (ii) a method of fixing the luer tip member on the mouth of the barrel (having the shape of a vial mouth) through packing by a caulking member of aluminum; and (iii) a method of press-fitting a rubber plug holding member with the luer tip of hard plastic of the mouth barrel.

In the method (i) comprising heating, melting and embossing the glass pipe, the sizing accuracy is poor, so that the portion to be fitted in partnership (such as the hub of a needle or a female luer connector) has to be polished for a higher sizing accuracy by means of a grinding stone. Furthermore, the polishing work is difficult to automate and requires checking of all the individual parts, so that the method is extremely low in productivity and high in cost.

In the method (ii), on the other hand, the caulking member is made from aluminium. When the luer tip member is wound around the mouth of barrel, therefore, fine powder of aluminium may be produced to contaminate the sterile room or to mix as a foreign substance into a medical liquid contained in the syringe. Another defect is that the aluminium member has to be separated and scrapped. Like the method (i) the method (iii) comprises a polishing treatment because it is necessary to have accurate sizing in the external diameter of the mouth of the barrel. Since the luer tip member of hard plastic (such as polycarbonate) is forcibly press-fitted problems are frequently encountered by cracking in the press-fitted portion of the rubber plug holder. In the case of a glass barrel, the tip is positioned on the centreline of the glass barrel. In a syringe having a capacity of 20 milliliters or more, generally, there is problem that the needle so positioned is hard to insert into a (human) body.

In order to solve the above-specified problems, a pre-filled syringe was proposed in Japanese Patent Application Laid-Open Nos. (a) Hei-07-80065 and (b) Hei-07-313596 (European Patent Application No. 685237, U.S. Pat. No. 5,624,405).

The former pre-filled syringe (a) comprises a barrel of glass; a tip member fitted liquid-tightly on a medical liquid discharge port at a distal end of the barrel; a sealing member for sealing the tip member and the medical liquid discharge port liquid-tightly: a cap-shaped member for caulking and fixing the sealing member on the medical liquid discharge port; and a sealing member for sealing a needle mounting portion of a distal end of the tip member, and is characterized in that the inside is filled with a medical liquid, and in that the proximal end opening of the barrel is closed by a plunger inserted liquid-tightly thereinto.

In this pre-filled syringe, however, the sealing member mounted on the needle portion of the tip member can be arbitrarily mounted/demounted to raise a problem that the medical liquid contained therein may be tampered with or contaminated.

The latter pre-filled syringe (b) comprises a barrel made of glass and having at the distal end thereof a medical liquid discharge port formed in the shape of a vial mouth; a sealing member fitted in the medical liquid discharge port of the barrel and having a through-hole in the axial direction; a tip member including a skirt provided with an engagement pawl on a lower end inner wall thereof, a top wall, a needle mounting portion and a medical liquid deriving portion and forming a medical liquid passage through the medical liquid deriving portion, the top wall and the needle mounting portion; a sealing member for sealing the needle mounting portion of the tip member; and a holding member for mounting and fixing the tip member on the medical discharge port of the barrel, and is characterized in that the tip member is mounted liquid-tightly on the medical liquid discharge port by mounting the holding member around the tip member and sliding downward along the skirt thereof.

However, the latter pre-filled syringe has a portion where the medical liquid and the tip member (of a thermoplastic resin) are in contact with each other, and a gas (e.g. oxygen) outside of the syringe may infiltrate from that portion into the medical liquid thereby raising the problem that the medical liquid deteriorates in potency, and may generate degradation by-products over time, if unstable in the presence of oxygen.

The present invention has however been conceived in view of the background thus far described and has an object to solve the above specified problems by improving, in particular, the pre-filled syringe of Japanese Patent Application Laid-Open No. Hei-07-313596.

We have keenly made investigations to solve those problems and found that the tampering and deterioration of a medical liquid can be simultaneously prevented if a closing member integrated with a cap member is inserted into a medical liquid passage of a tip member and a through-hole of a sealing member thereby to close the through-hole, According to the invention, more specifically, there is provided a pre-filled syringe comprising: a barrel made of glass and having at a distal end thereof a medical liquid discharge port formed into the shape of a vial mouth; a sealing member fitted in the medical liquid discharge port of the barrel and having a through-hole in the axial direction; a tip member including a skirt provided with an engagement pawl on a lower end inner wall thereof, a top wall, a needle mounting portion and a medical liquid deriving portion and forming a medical liquid passage through the medical liquid deriving portion, the top wall and the needle mounting portion, and so mounted around the sealing member on the medical liquid discharge port of the barrel as to slide along the outer wall of the medical liquid discharge port; a cap member mounted around the tip member; a closing member made integral with the cap member and inserted into the medical liquid passage of the tip member and the through-hole of the sealing member for closing the through-hole; and a holding member for mounting and fixing the tip member on the medical liquid discharge port of the barrel, wherein the tip member is mounted liquid-tightly on the medical liquid discharge port by mounting the holding member around the tip member and sliding downward along the skirt of the tip member to bring the enagement pawl of the tip member into engagement with the medical liquid discharge port of the syringe.

Here, the sealing member may be a rubber plug having an annular rib on the top wall thereof so as to regain the liquid-tightnesss of the medical liquid passage. On the other hand, it is preferable that the tip member is provided on the skirt thereof with an axial slit so as to facilitate an inward flexure and at the outer wall of a lower end portion thereof with retaining means for engaging with the holding member. It is preferable that the needle mounting portion includes an inner side tip and outer side female joint means which are concentrically protruded on the outer side of the top wall of the tip member. On the other hand, the needle mounting portion may be positioned eccentric from the axis of the tip member. The holding member may be provided at the lower end inner wall thereof with a skirt having an engagement pawl for engaging with the retaining means of the tip member, and a top wall having a hole. It is preferable that the cap member includes concentric inner and outer caps which are mounted around the tip of the needle mounting portion and the female joint means, respectively.

In the case of the cap member including the inner cap and the outer cap, the holding member is temporarily assembled with the upper end portion of the skirt of the outer cap, so that the engagement pawl of the tip member can be brought into engagement with the medical liquid discharge port of the syringe by sliding the holding member downward along the outer cap and the skirt of the tip member.

The pre-filled syringe of the present invention may have tampering prevention. Therefore, for example, the outer cap may be provided with a flange at a skirt lower end portion and the flange removably held between the top wall of the holding member and top wall of the tip member. In this case, the flange may be provided with a fragile portion and the flange may be broken at the fragile portion when the cap member is removed. On the other hand, the flange may be formed thin and the flange may be transformed and come off between the top wall of the holding member and the top wall of the tip member when the cap member is removed. The flange may be provided a fanwise slit. On the other hand, it is preferable that the outer cap is covered with a cylindrical cover cap which connects with the top wall of the holding member through the fragile portion, and the cylindrical cover cap can be broken from the top wall of the holding member for the tampering prevention. In this case, the cap member may be removed with the cylindrical cover cap.

The invention is now illustrated, but not limited, by reference to the following embodiments of the invention which are described with reference to the accompanying drawings.

Figure 1:
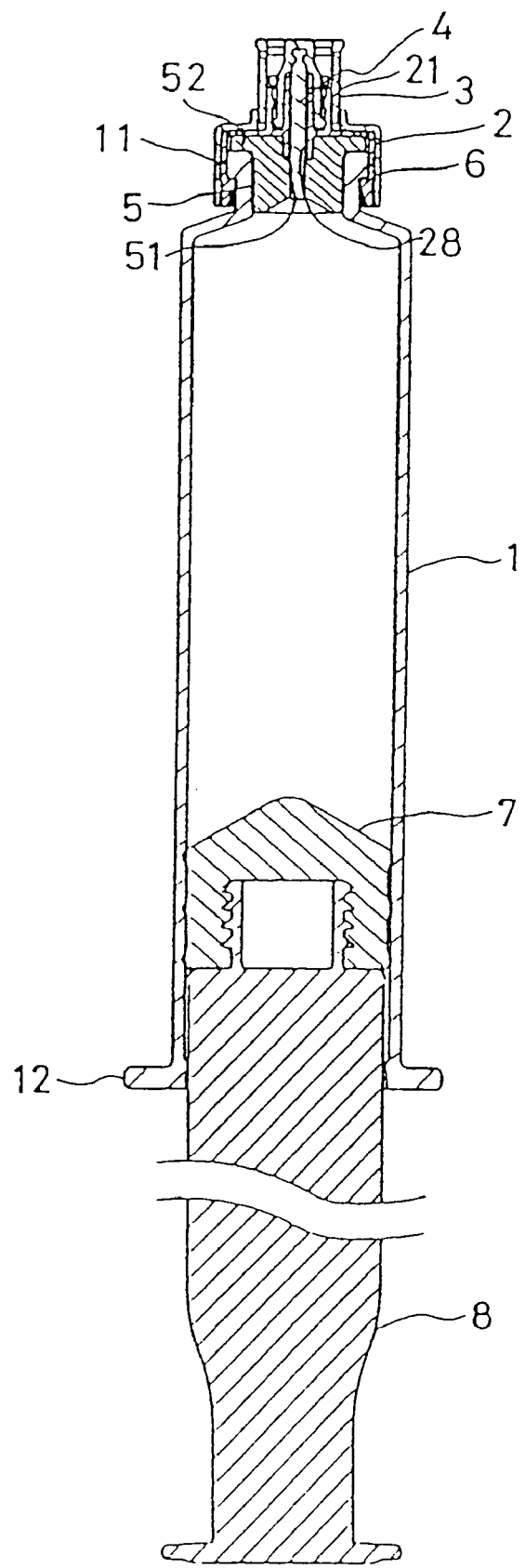
FIG. 1 is a longitudinal section view showing one embodiment of the invention.
Figure 18:
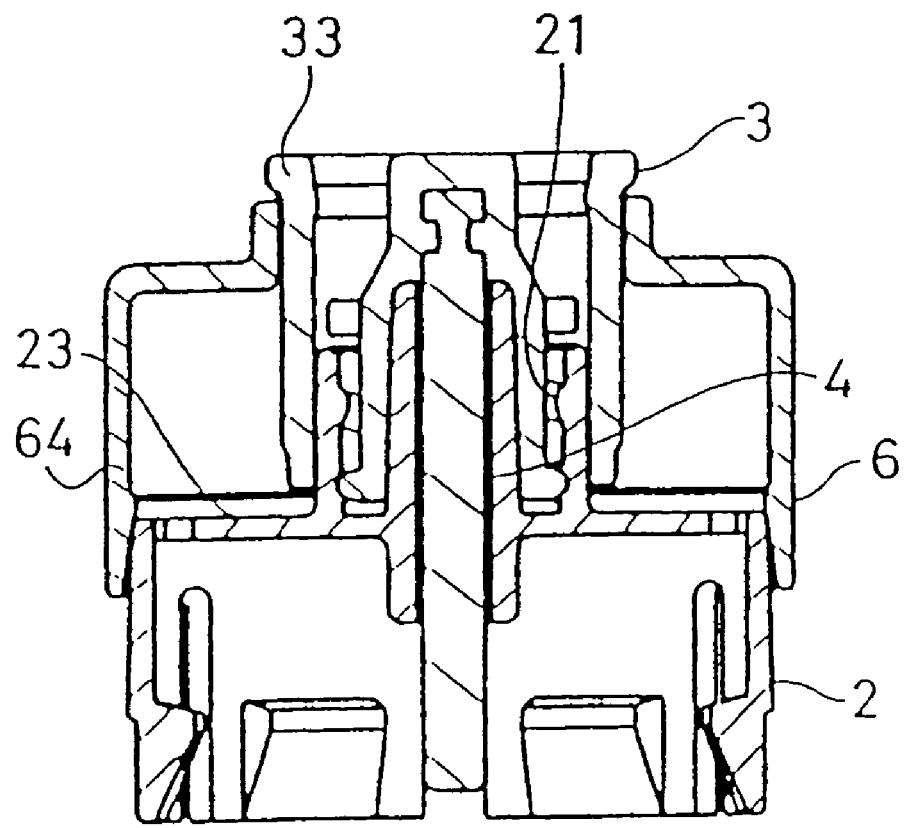

FIG. 18 is an explanatory view showing relations among the tip member, the cap member, the closing member and the holding member shown in FIG. 1 and shows a state before they are mounted on a medical liquid discharge port of a barrel. On the other hand, FIGS. 19 to 22 are explanatory views of a method of attaching the sealing member, the tip member, the cap member, the closing member and the holding member to the medical liquid discharge port of the barrel.

Figure 2:
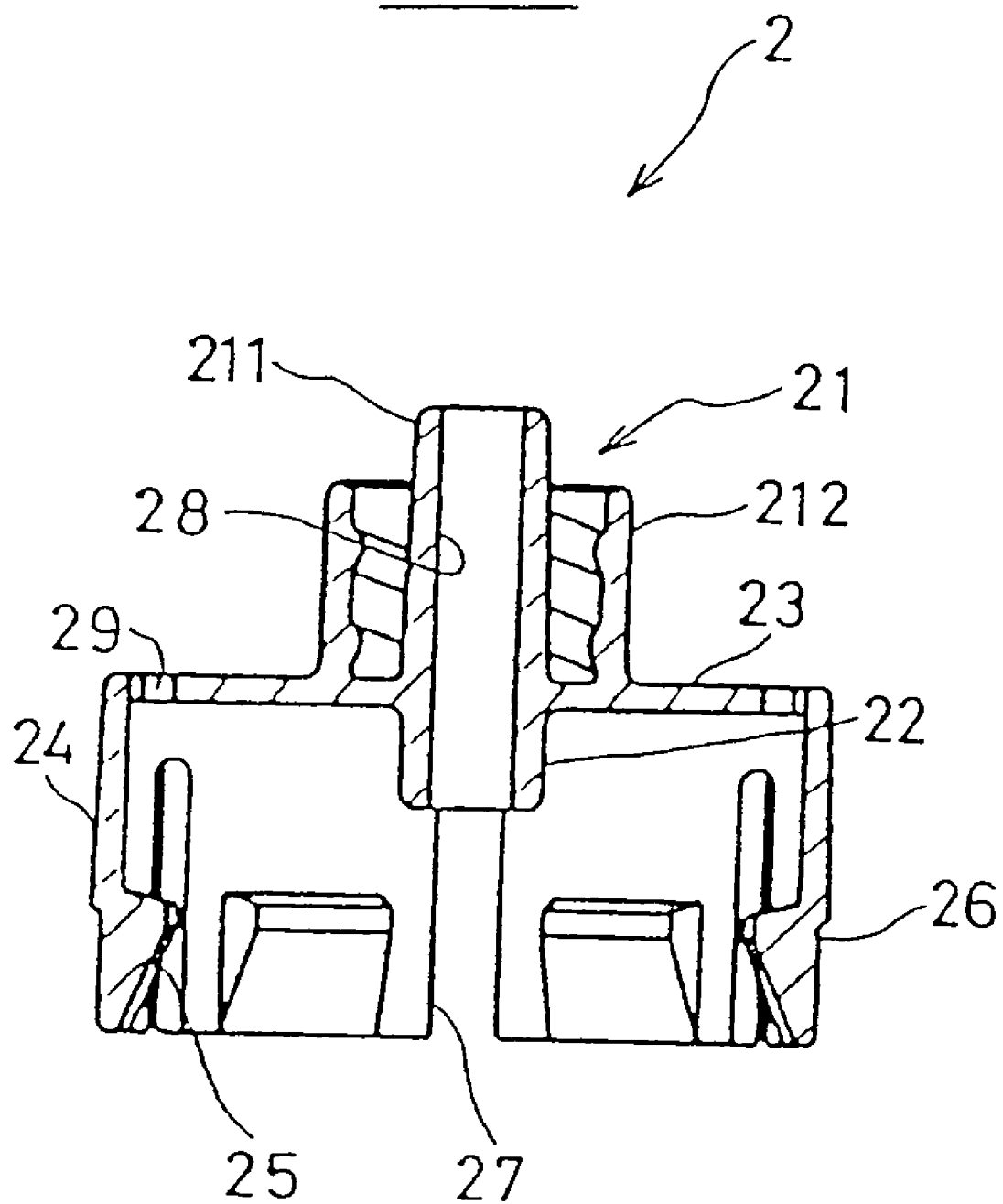
FIG. 2 is an enlarged section view of a tip member shown in FIG. 1.

Referring now to FIG. 1, there is shown a pre-filled syringe according to the present invention. The pre-filled syringe comprises a barrel (1) made of glass, a sealing member (5) fitted in a medical liquid discharge port (11) of the barrel (1), a tip member (2) mounted around the sealing member (5) on the medical liquid discharge port (11) of the barrel (1), a closing member (4), a cap member (3), and a holding member (6). The sealing member (5) has a through-hole (51) formed in the axial direction. The tip member (2) includes a skirt (24) provided with an engagement pawl or projection (25) on the inner wall of a lower end thereof, a top wall (23), a needle mounting portion (21), and a medical liquid deriving portion (22), and is provided with a medical liquid passage (28), as shown in FIG. 2. The closing member (4) is inserted into the medical liquid passage (28) and the through-hole (51) to close the through-hole (51). The tip member (2) can be mounted liquid-tight on the medical liquid discharge port (11) by mounting the holding member (6) around the tip member (2) and by sliding the holding member (6) downward along the skirt (24) of the tip member (2) to bring the engagement pawl (25) of the tip member (2) into engagement with the medical liquid discharge port (11).

The barrel (1) is a container made of glass and having two open ends, and the medical liquid discharge port (11) at a distal end thereof is formed into a shape like that of a vial mouth and a side wall of the medical liquid discharge port (11) is annularly bulged at a distal end thereof, and is formed into a flange (12) at a proximal end thereof. The barrel (1) is filled with a (not-shown) medical liquid and is closed at a proximal end opening thereof with a gasket (7) inserted liquid-tightly thereinto. This gasket (7) is made slidable in the bore of the barrel, and a plunger (8) is (or can be) coupled to the proximal end thereof. This gasket (7) is ordinarily made of a rubbery elastic material such as natural rubber or synthetic rubber (e.g. butyl rubber or isoprene rubber), or a thermoplastic elastomer.

Figure 5:
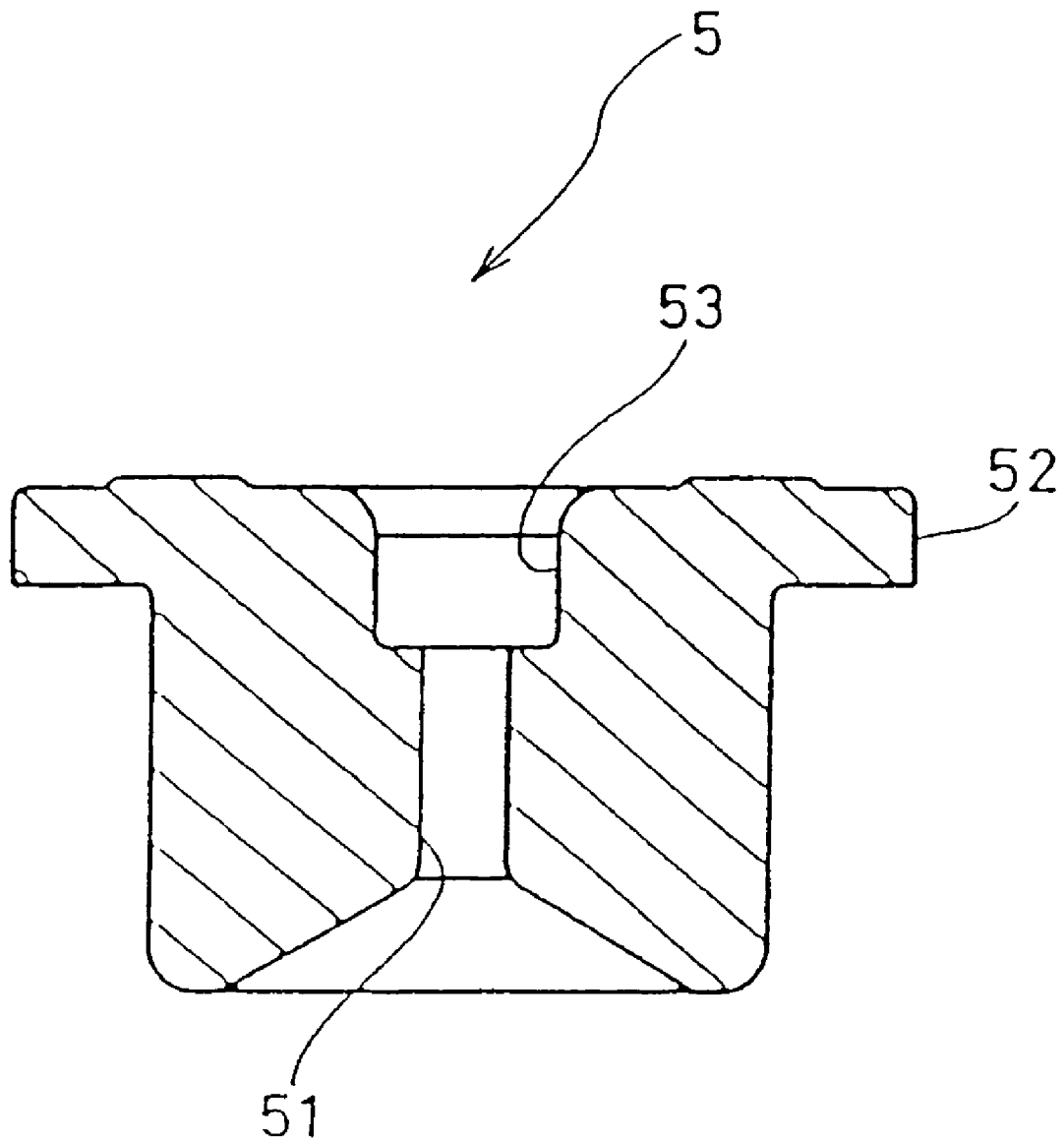
FIGS. 5 and 6 are enlarged section views of a sealing member and a holding member.
Figure 7:
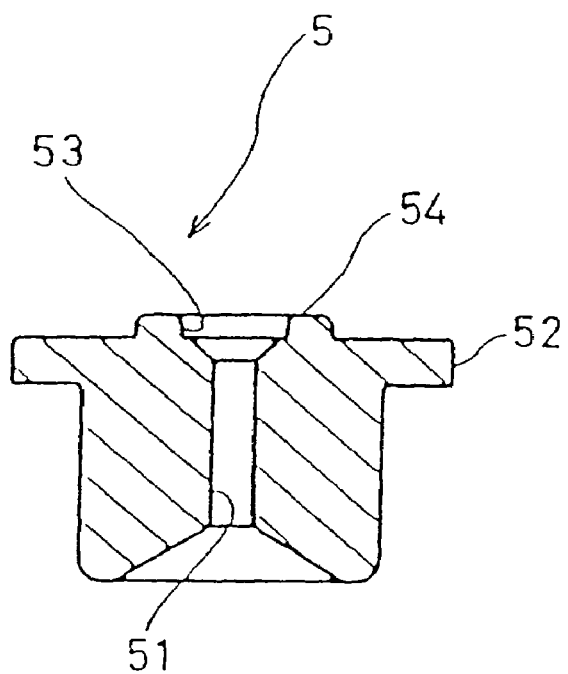
FIG. 7 is a longitudinal section view showing another embodiment of the sealing member.

In the medical liquid discharge port (11) at a distal end of the barrel (1), there is mounted a rubber plug (5) as the sealing member. This rubber plug (5) is made of a material similar to that of the gasket (7) and is provided at a top wall thereof with a flange (52) for sealing a distal end face of the medical liquid discharge port (11) and in the axial direction with the through-hole (51) as shown in FIG. 5. Into this through-hole (51), there is inserted liquid-tightly the closing member (4), as will be described hereinafter. The through-hole (51) is radially extended on a top wall side thereof to form a recess (53), in which the medical liquid deriving porition (22) of the later-described tip member (2) is inserted liquid-tightly. The rubber plug (5) may be provided with an annular rib (54), as shown in FIG. 7, so as to retain the liquid-tightness of the medical liquid passage of the later described tip member (2).

The tip member (2) is mounted over the rubber plug (5) on the medical liquid discharge port (11) of the barrel (1) to push the flange (52) of the rubber plug (5) on the medical liquid discharge port (11). Generally, the tip member (2) is made of a flexible resin such as polypropylene, polyethylene, cyclic olefin copolymer or an ABS resin. Referring now to FIG. 2, the tip member (2) includes the top wall (23), the skirt (24), the needle mounting portion (21) protruded outward of the top wall (23), and the medical liquid deriving portion (22) protruded outward. The tip member (2) can slide along the outer wall of the medical liquid discharge port (11). The skirt (24) is gently diverged downward in a taper shape and is provided at a lower end inner wall and at a lower end outer wall thereof, respectively, with the engagement pawl (25) for engaging with the medical liquid discharge port (11) and retaining means (26) for engaging with an engagement pawl or projection (64) of the later-described holding member (6). The skirt (24) is preferably provided in an axial direction thereof with one or more slits (27) so that it can warp outward. The preferable member of the slits (27) is three or four. The medical liquid passge (28) is formed through the medical liquid deriving portion (22), the top wall (23) and the needle mounting portion (21) so that the medical liquid, as contained in the barrel (1), is ejected by way of that medical liquid passage (28). The needle mounting portion (21) is a piped protuberance (or tip (211)) provided with the medical liquid passage (28) and is ordinarily converged toward the distal end in a taper shape. The needle mounting portion (21) is preferred to have the so-called "luer lock type" composed of the concentric inner tip (211) and outer female joint means (212), as shown in FIG. 2. In this case, the medical liquid passage (28) is closed by an inner cap (32) of the later-described cap member (3) to be mounted around the tip (211). In the case of a barrel having a large capacity, the needle mounting portion (21) and the medical liquid deriving portion (22) may be formed eccentric with respect to the axis of the tip member (2) so that the needle may be easily inserted into the skin of a patient.

The engagement pawl (25) on the lower end inner wall of the skirt (24) comes into engagement with the medical liquid discharge port (11) when the tip member (2) slides along the outer wall of the medical liquid discharge port (11) of the barrel (1) and reaches a slide end point. On the other hand, the retaining means (26) at the lower end outer wall of the skirt (24) comes into engagement with the engagement pawl (64) of the holding member (6) when the holding member (6) slides along the skirt (24) of the tip member (2) and reaches a slide end point.

If necessary, the top wall (23) may be provided with an extracting window (29) at moulding time, and the skirt (24) may also be provided at an upper portion thereof with a (not shown) shallow engagement groove for removably engaging with the engagement pawl (64) of the holding member (6), so that the holding member (6) may be placed in the state mounted on the tip member (2). If, in this case, the holding member (6) and the cap member (3) are mounted on the tip member (2), the tip member (2) and the holding member (6) can be mounted on the medical liquid discharge port (11) of the barrel (1) by a single action.

Figure 3:
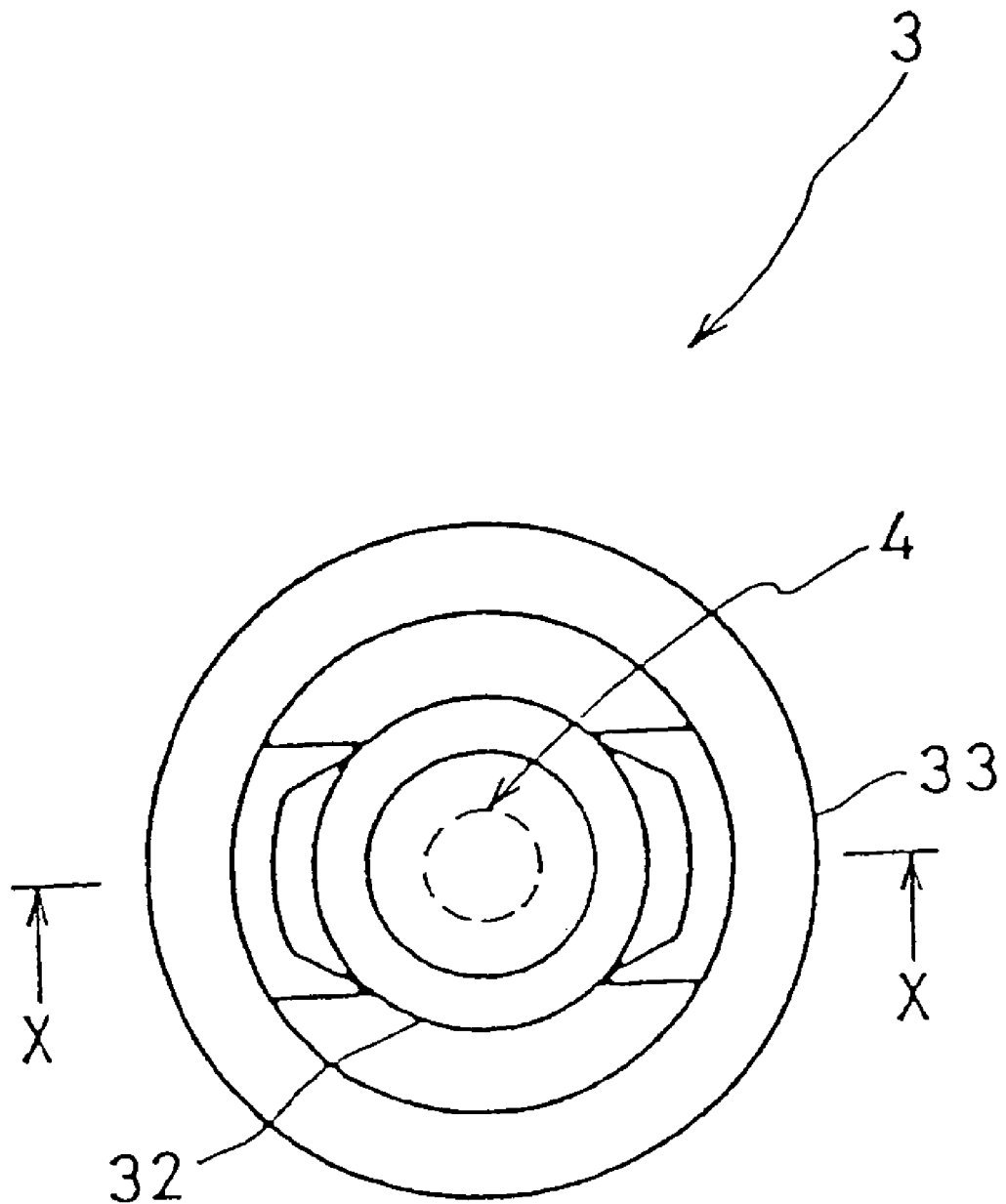
FIG. 3 is an enlarged top plan view of an integral structure of a cap member and a closing member shown in FIG. 1.
Figure 4:
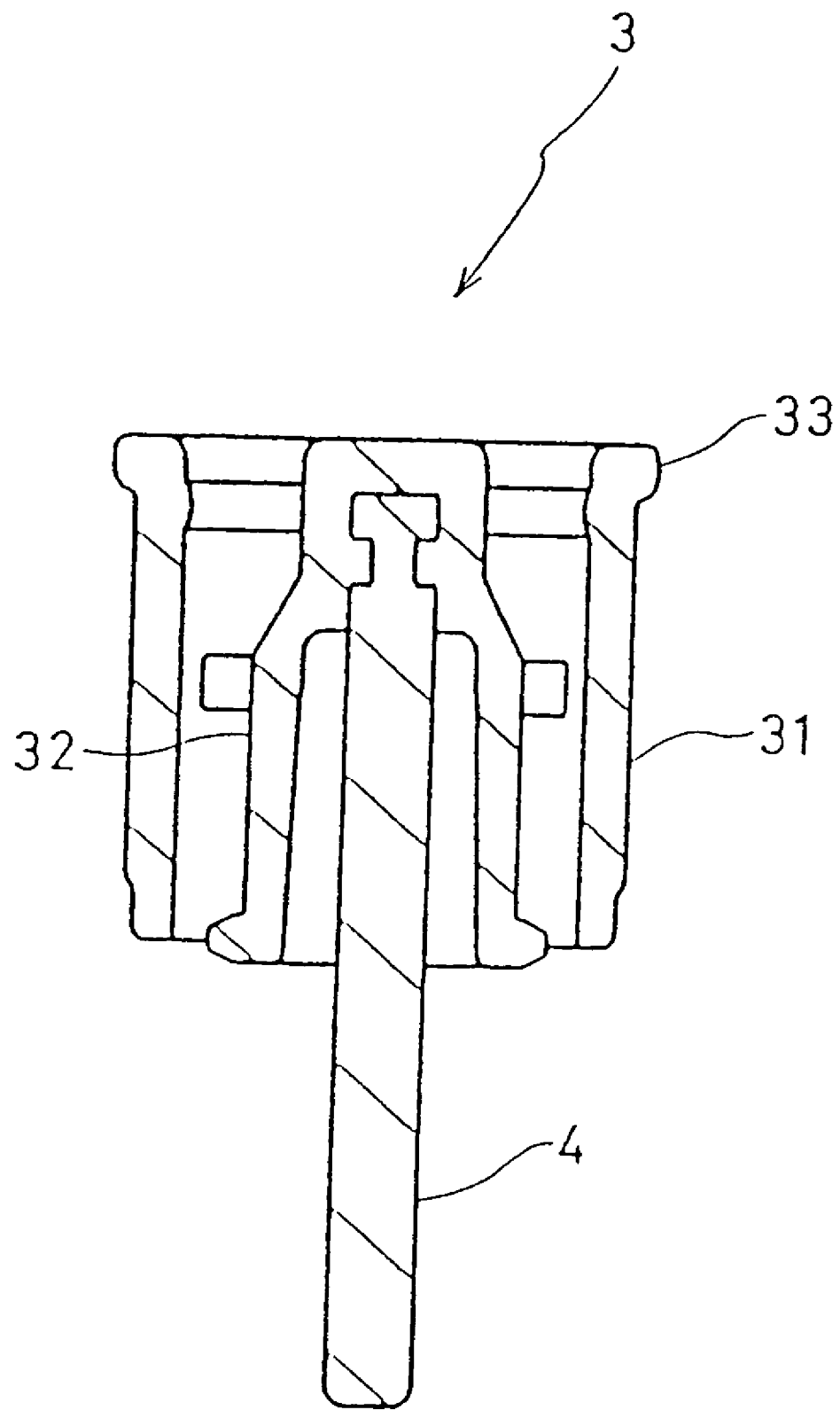
FIG. 4 is a section view along line X—X of FIG. 3.

The cap member (3) is fitted on the needle mounting portion (21) of the tip member (2), and the closing member (4) is integrally mounted on the inner side of the top wall of the cap member (3) either by the integral moulding (or insert moulding) method or by the jointing method. The cap member (3) is generally made of a flexible resin such as polypropylene, polyethylene, cyclic olefin copolymer or an ABS resin, and the closing member (4) to be integrated with the former is generally made of stainless steel or glass having excellent gas barrier properties. When the needle mounting portion (21) of the tip member (2) is of the luer lock type, the cap member (3) adopted is composed of an outer cap (31) and the inner cap (32) which are made concentric, as shown in FIGS. 3 and 4. In the cap member (3) of this type, the closing member (4) is mounted on the inner cap (32). The outer cap (31) is provided at a top wall thereof with an annular ridge (33) so that the upper end portion of the holding member (6) is temporarily fixed adjacent to the annular ridge (33) when the tip member (2), the holding member (6) and the cap member (3) are temporarily assembled, as shown in FIG. 18. The closing member (4) has a slightly larger external diameter than that of the through-hole (51) of the sealing member (5) so that it is inserted, when the cap member (3) is assembled with the medical liquid discharge port (11) of the barrel (1), into the through-hole (51) of the sealing member (5) to shield the medical liquid contained in the barrel (1) from the atmosphere.

Figure 6:
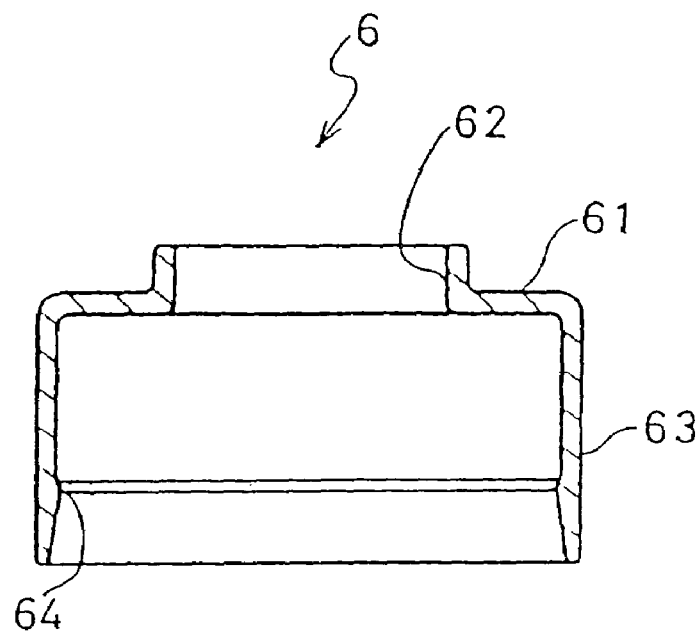

On the tip member (2) fitting the cap member (3) on a needle mounting portion (21), here is mounted the holding member (6) over the cap member (3). The holding member (6) is made of a synthetic resin similar to that of the tip member (2) and is composed of the top wall (61) having a hole (62) and a skirt (63), as shown in FIG. 6. When the holding member (6) slides downward along the outer wall of the skirt (24) of the tip member (2), the skirt (24) is pushed to warp inward to bring an engagement pawl (25) into engagement with the medical liquid discharge port (11) of the barrel (1). On the other hand, an engagement pawl (64) which is formed on the lower end inner wall of the holding member (6) comes into engagement with the retaining means (e.g. undercut) (26) formed in the lower end outer wall of the tip member (2), at a position where the inner side of the top wall (61) of the holding member (6) abuts against the top wall (23) of the tip member (2). The holding member (6) is temporarily mounted, when it is temporarily assembled with the tip member (2) and the cap member (3), as shown in FIG. 18, an upper end portion thereof at the position adjacent to the annular ridge (33) of the cap member (3), as described hereinbefore, and at the engagement pawl (64) of a lower end portion thereof with the top wall (23) of the tip member (2). At the temporarily assembling time, therefore, the holding member (6) can be temporarily assembed with the cap member (3) and the tip member (2) to expect an effect that the number of part feeders can be reduced at the manufacturing time, for example.

Figure 8:
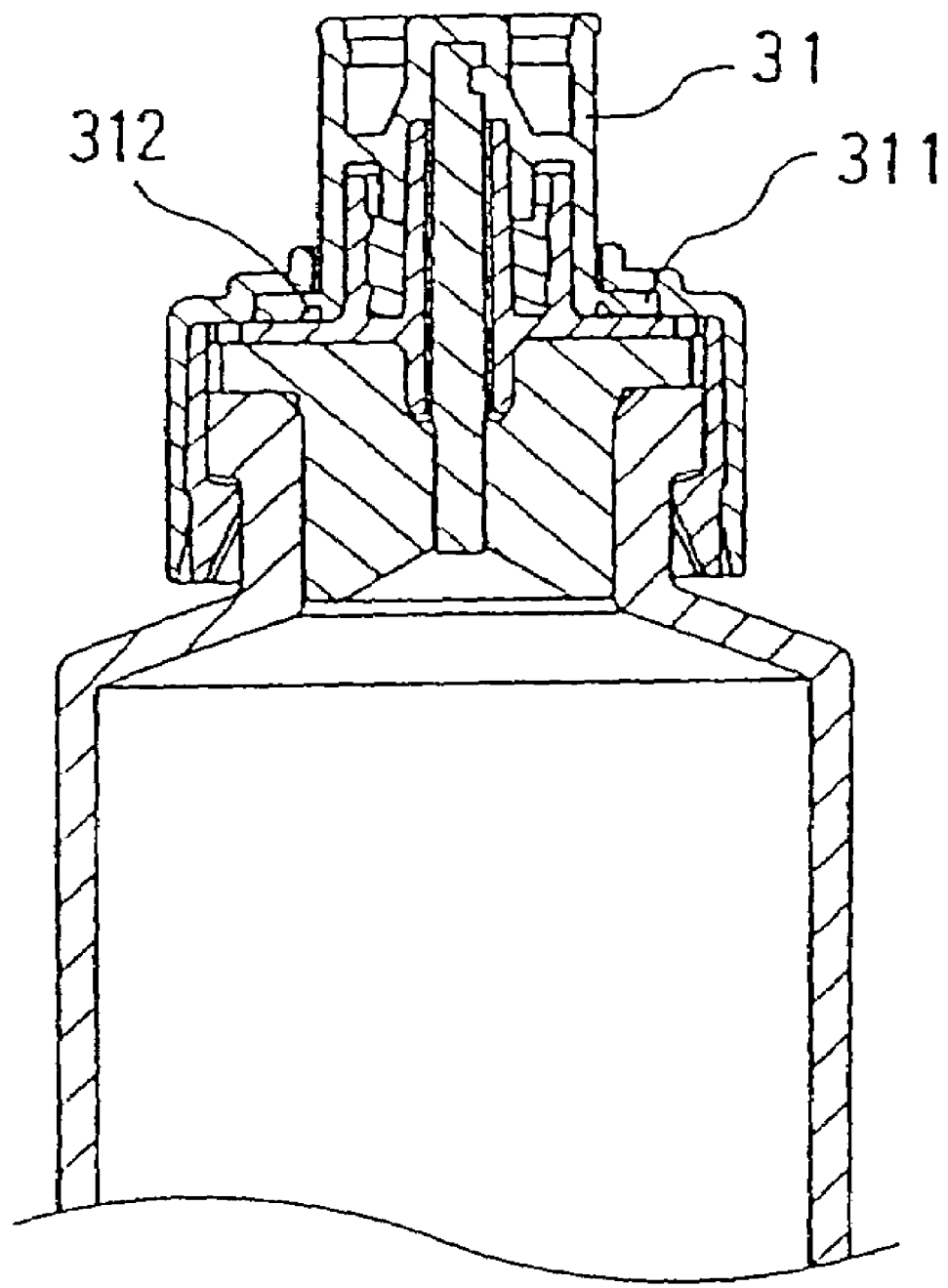
FIGS. 8 to 10 are longitudinal section views showing other embodiments of the invention.
Figure 9:
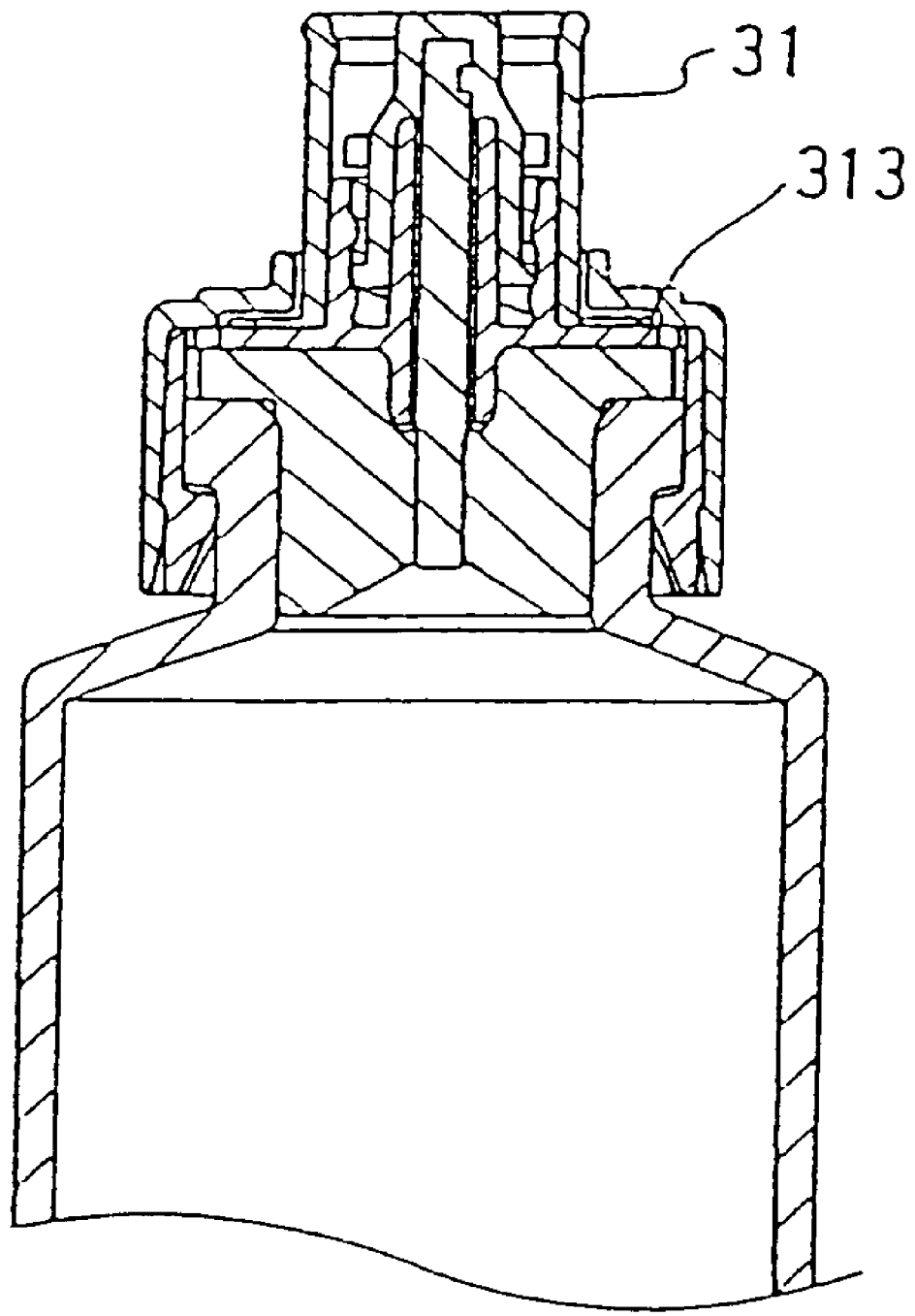
Figure 10:
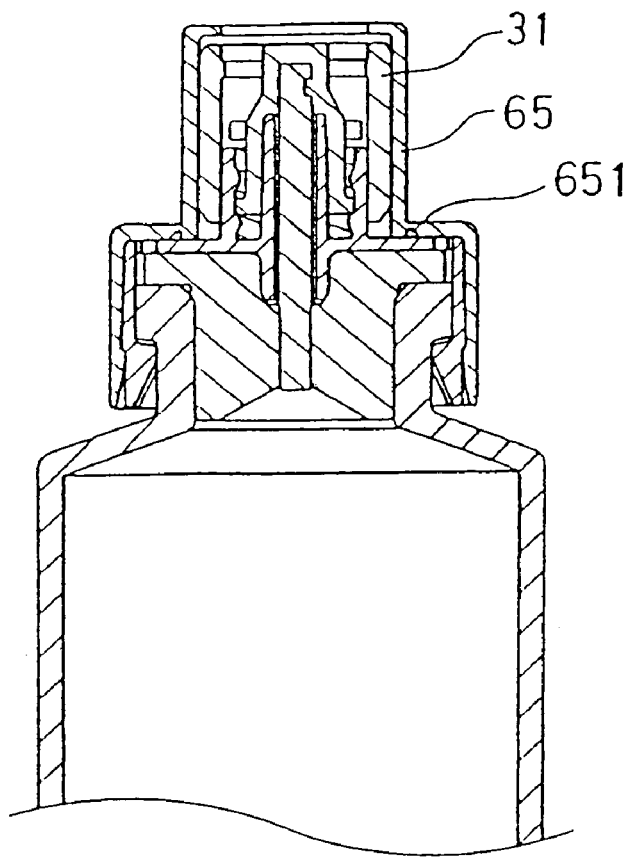

The pre-filled syringe of the present invention may have the tampering prevention as shown in FIG. 8 to 10.

The outer cap (31) is provided with a flange (311) at a skirt lower end portion and the flange (311) removably held between the top wall (61) of the holding member (6) and the top wall (23) of the tip member (2), as shown in FIG. 8. The flange (311) is provided with a fragile portion (312) shown in FIG. 11 for example and the flange (311) is broken at the fragile portion (312) when the cap member (3) is removed.

Figure 12:
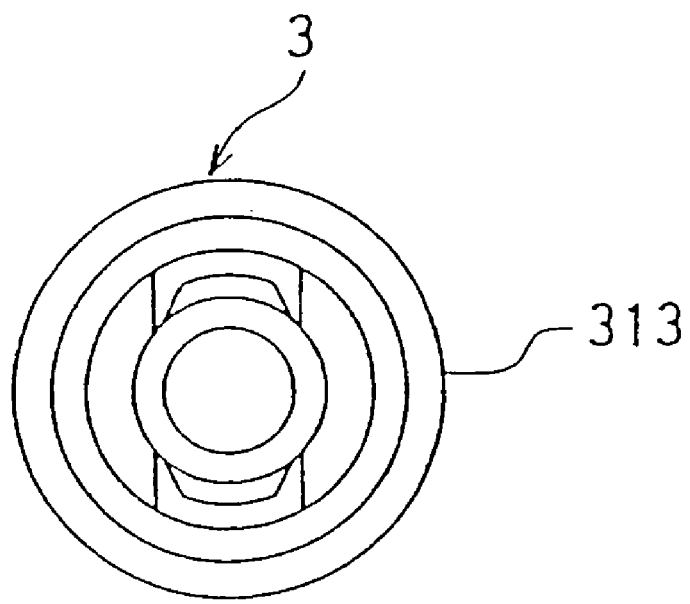
FIGS. 12 to 14 are top plan views of the embodiments of the cap member shown in FIG. 9.
Figure 13:
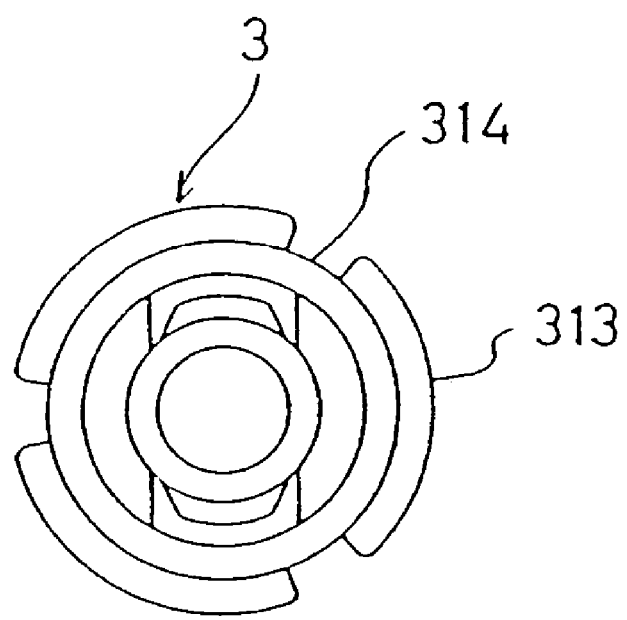
Figure 14:
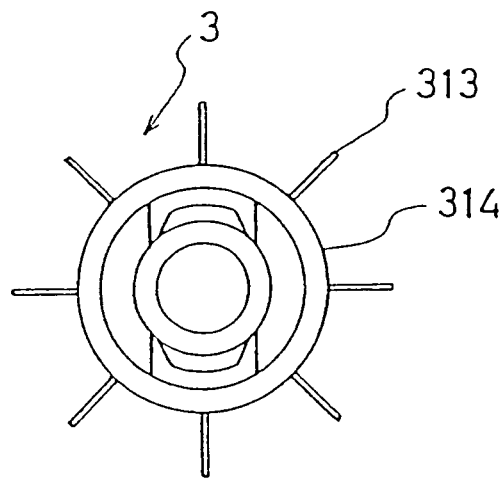

FIG. 9 shows the outer cap (31) in which the flange (313) is formed thin for giving flexibility in the same composition as FIG. 8. The flange (313) is transformed and comes off between the top wall (61) of the holding member (6) and the top wall (23) of the tip member (2) when the cap member (3) is removed. Here, the flange (313) may be formed as shown in FIG. 12. In this case, the intervals of the top wall (61) of the holding member (6) and the top wall (23) of the tip member (2) are made a little wider than the thickness of the flange (313) for transforming of the flange (313). In the case when the intervals of the top wall (61) of the holding member (6) and the top wall (23) of the tip member are made of similar thickness to the flange (313), the flange (313) may be provided with a fanwise slit (314) as shown in FIG. 13, and in an extreme case, the flange (313) may be formed as shown in FIG. 14.

Figure 15:
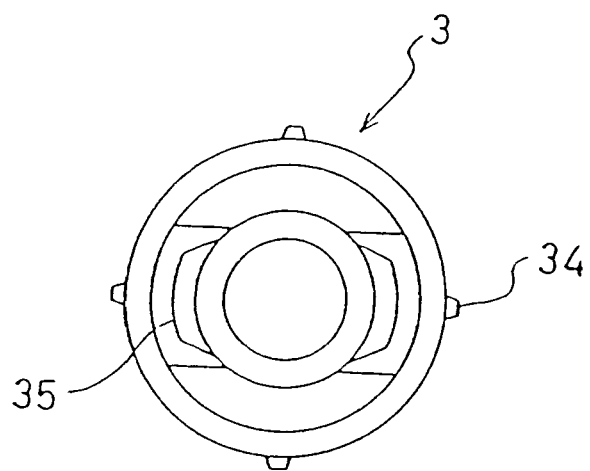
FIG. 15 is a top plan view of a cap member shown in FIG. 10.
Figure 16:
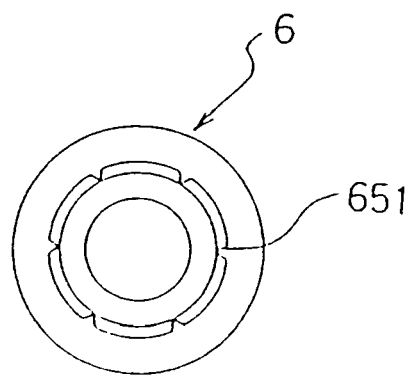
FIG. 16 is a top plan view of the holding member shown in FIG. 10.
Figure 17:
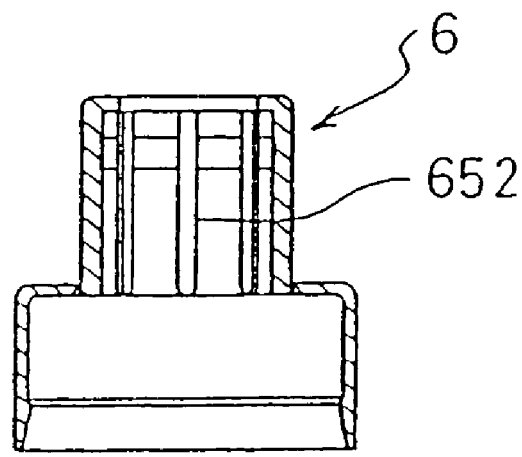
FIG. 17 is a longitudinal section view of the holding member shown FIG. 10.

FIG. 10 shows that the outer cap (31) is covered with a cylindrical cover cap (65) which connects with the top wall (61) of the holding member (6) through the fragile portion (651) as shown in FIG. 16 for example, and the cylindrical cover cap (65) can be broken from the top wall (61) of the holding member (6) for tampering prevention/tamper-proof evidence. In this case, the cap member (3) and the holding member (6) are formed respectively such as FIG. 15, FIG. 16 and FIG. 17, and the cap member (3) and the cylindrical cover cap (65) may be removed from the tip member (2) together. In this composition, the cap member (3) is connected with tip (211) by male joint means (35) which are provided on miner cap (32) as shown in FIG. 15. The holding member (6) is turned in the direction where the combination of the inner cap (32) and the top (211) is cancelled, the cylindrical cover cap (65) is broken first from the top wall (61) in the fragile portion (651). After this, the longitudinal ribs (652) which are provided at the outside wall of the outer cap (31) of the cap member (3) as shown in FIG. 17 are engaged with the longitudinal ribs (34) which are provided at the inside wall of the cylindrical cap (65) of the holding member (6) as shown in FIG. 15, the cap member (3) is rotated with the cylindrical cover cap (65) and the cap member (3) is removed from the tip member (2).

The assembly of the pre-filled syringe of the invention is now described with reference to FIGS. 19 to 22.

FIG. 18 shows the state (or the temporary assembly of the tip member and so on) in which the integral structure of the cap member (3) and the closing member (4) are mounted on the needle mounting portion (21) of the tip member (2) after the holding member (6) was lightly mounted around the tip member (2).

Figure 19:
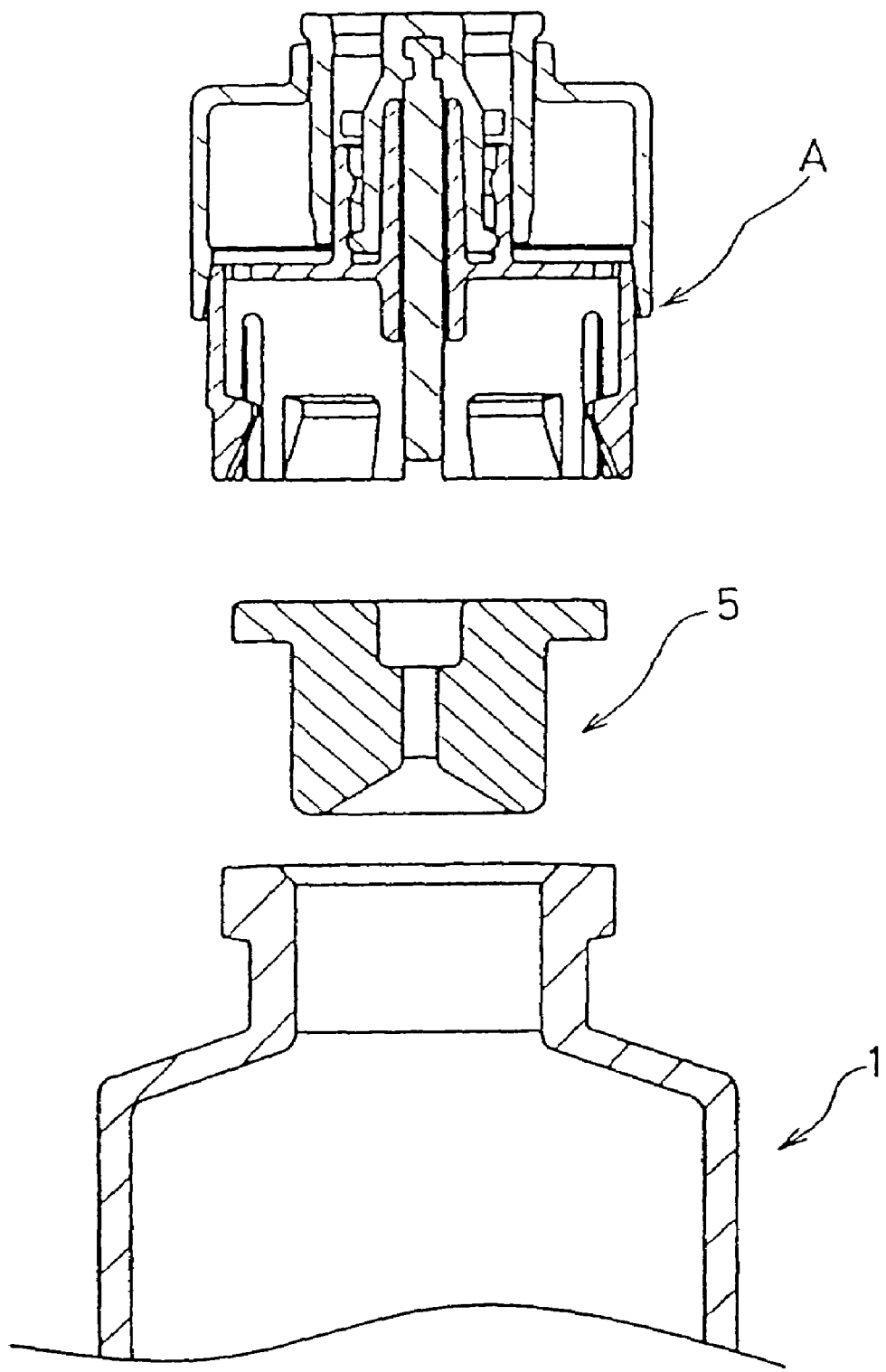
Figure 20:
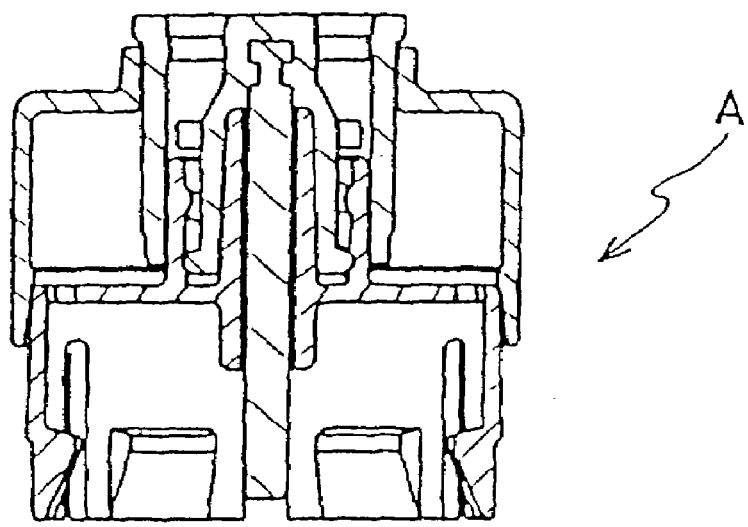
Figure 20:
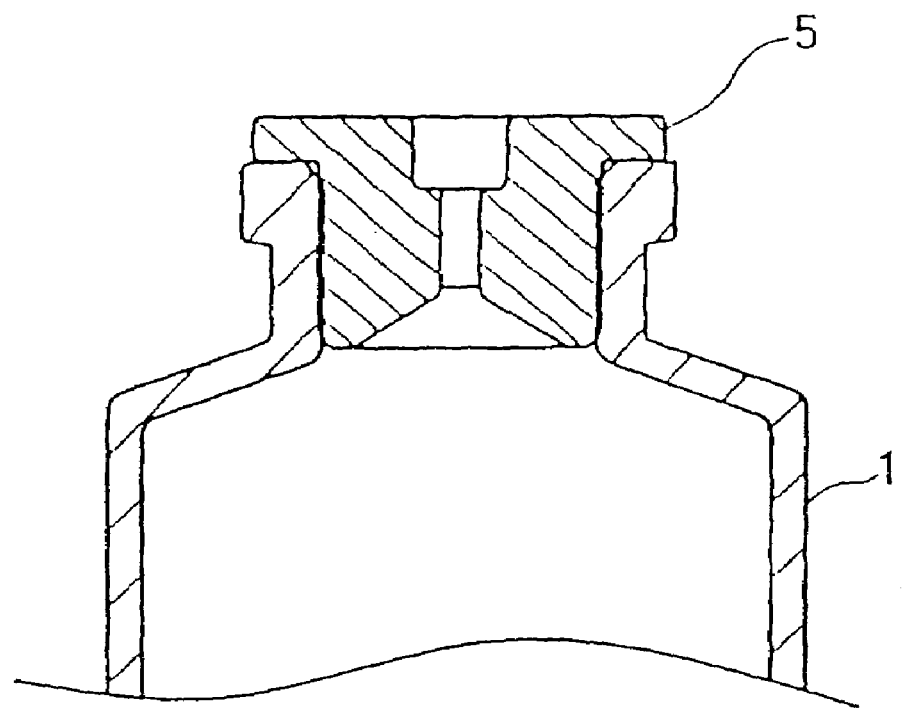
Figure 21:
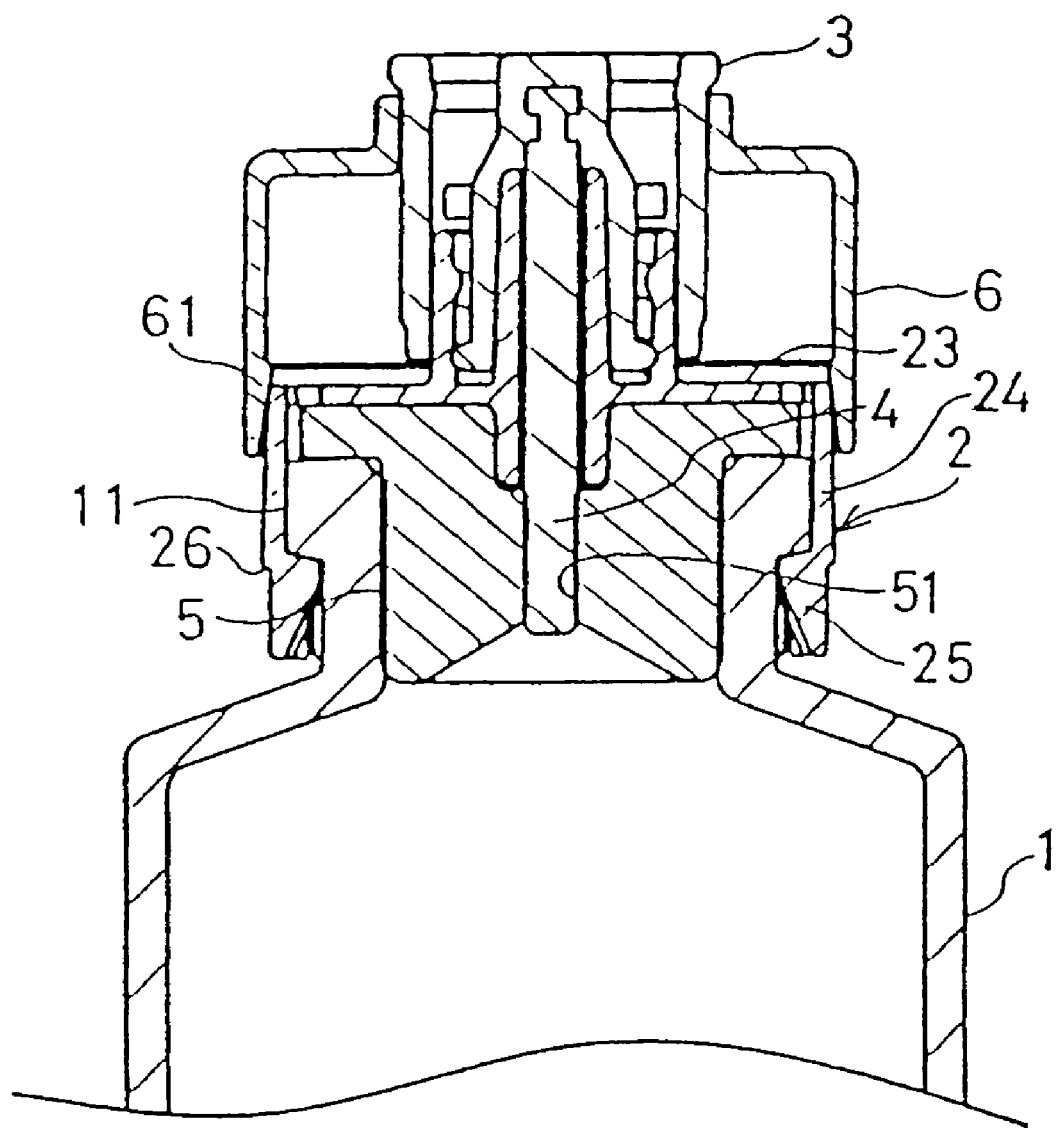
Figure 22:
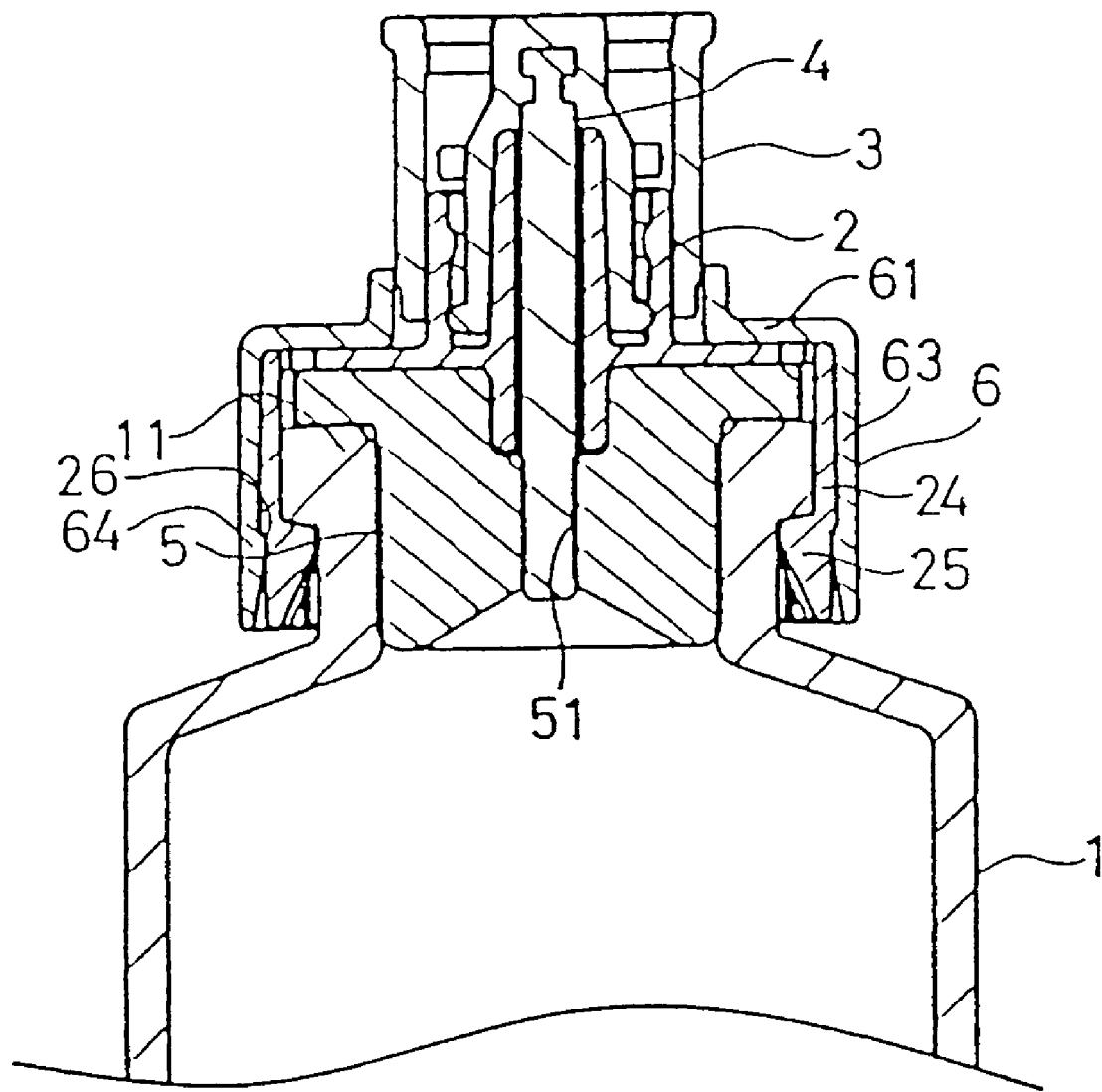

First of all, there is prepared a temporary assembly A of the barrel (1), the sealing member (5), the tip member and so on, as shown in FIG. 19. The sealing member (5) is inserted into the medical liquid discharge port (11) of the barrel (1), as shown in FIG. 20. After this, the temporary assembly A of the tip member and so on is applied to the medical liquid port (11) and is pushed downward. Then, the tip member (2) is moved downward along the medical liquid discharge port (11) until it is stopped at a position, as shown in FIG. 21. At this time, the cap member (3) and the closing member (4) are moved downward together with the tip member (2) so that the closing member (4) is inserted liquid-tightly into the through-hole (51) of the sealing member (5). When the downward movement of the tip member (2) stops, moreover, the holding member (6) slides along the outer wall of the skirt (24) of the tip member (2) to deform the skirt (24) inward thereby to bring an engagement pawl (25) into firm engagement with the medical liquid discharge port (11). The movement of the holding member (6) stops at the position where a top wall (61) abuts against the top wall (23) of the tip member (2), so that an engagement pawl is firmly fixed on the medical liquid discharge port (11) (as shown in FIG. 22) while engaging with the retaining means (26) of tip member (2).

As is apparent from the above description, the pre-filled syringe of the invention is constructed such that the through-hole of the sealing member is closed by the closing member having high gas barrier properties. This construction makes it possible to improve the sealing properties far better than those of the prior art and to apply the pre-filled syringe even to medical agents unstable to gases such as oxygen.

Also provided by the invention is a pre-filled syringe substantially as described herein and with reference to the Figures. Also provided as feature of the invention is a method of preventing contamination and deterioration of a medical liquid by use of a pre-filled syringe of the invention.

BRIEF DESCRIPTION OF THE DRAWINGS/FIGURES

[FIG. 1] A lontitudinal section view showing one embodiment of the invention.

[FIG. 2] An enlarged section view of a tip member shown in FIG. 1.

[FIG. 3] An enlarged top plan view of an integral structure of a cap member and a closing member shown in FIG. 1.

[FIG. 4] A section view along line X—X of FIG. 3.

[FIG. 5] An enlarged section view of a sealing member shown in FIG. 1.

[FIG. 6] An enlarged section view of a holding member shown in FIG. 1.

[FIG. 7] A longitudinal section view showing another embodiment of the sealing member.

[FIG. 8] A longitudinal section view showing another embodiment of the present invention.

[FIG. 9] A longitudinal section view showing another embodiment of the present invention.

[FIG. 10] A longitudinal section view showing another embodiment of the present invention.

Figure 11:
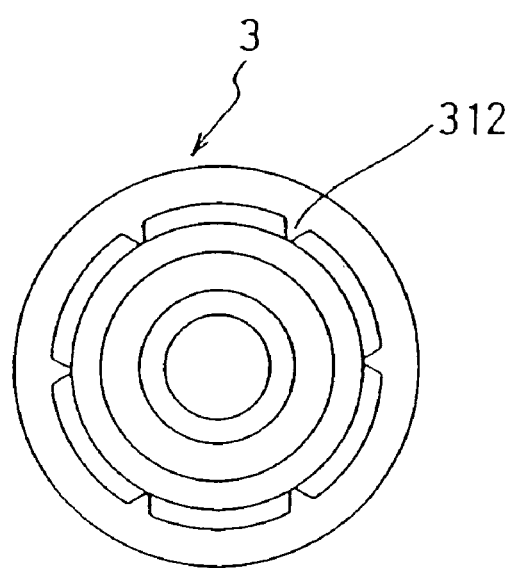
FIG. 11 is a top plan view of a cap member shown in FIG. 8.

[FIG. 11] A top plan view of a cap member shown in FIG. 8.

[FIG. 12] A top plan view of the embodiment of the cap member shown in FIG. 9.

[FIG. 13] A top plan view of the embodiment of the cap member shown in FIG. 9.

[FIG. 14] A top plan view of the embodiment of the cap member shown in FIG. 9.

[FIG. 15] A top plan view of a cap member shown in FIG. 10.

[FIG. 16] A top plan view of the holding member shown in FIG. 10.

[FIG. 17] A longitudinal section view of the holding member shown FIG. 10.

[FIG. 18] An explanatory view showing the relations among the tip member, the cap member, the closing member and the holding member shown in FIG. 1, and showing a state before they are mounted on a medical liquid discharge port of a barrel.

[FIGS. 19–22] An explanatory view of a method for mounting the sealing member, the tip member, the cap member, the closing member and the holding member on the medical liquid discharge port of the barrel.

| Key to Figures | |
| --- | --- |
| 1 | barrel |
| 11 | medical liquid discharge port |
| 12 | flange |
| 2 | tip member |
| 21 | needle mounting portion |
| 211 | tip |
| 212 | female joint means |
| 22 | medical liquid deriving means |
| 23 | top wall |
| 24 | skirt |
| 25 | engagement pawl |
| 26 | retaining means |
| 27 | slit |

-continued

Key to Figures

| | |
|---|---|
| 28 | medical liquid passage |
| 3 | cap member |
| 31 | outer cap |
| 311 | flange |
| 312 | fragile portion |
| 313 | flange |
| 314 | fanwise slit |
| 32 | inner cap |
| 33 | annular ridge |
| 4 | closing member |
| 5 | sealing member |
| 51 | through hole |
| 52 | flange |
| 53 | recess |
| 54 | annular rib |
| 6 | holding member |
| 61 | top wall |
| 62 | hole |
| 63 | skirt |
| 64 | engagement pawl |
| 65 | cylinderical cover cap |
| 651 | fragile portion |
| 652 | longitudinal rib |
| 7 | gasket |
| 8 | plunger |
| A | temporary assembly of tip member etc. |

The invention claimed is:

1. A pre-filled syringe comprising a barrel made of glass and having at a distal end thereof a medical liquid discharge port formed into the shape of a vial mouth; a sealing member fitted in the medical liquid discharge port of said barrel and having a through-hole in the axial direction; a tip member including a skirt provided with an engagement pawl on a lower end inner wall thereof, a top wall, a needle mounting portion and a medical liquid deriving portion and forming a medical liquid passage through said medical liquid deriving portion, said top wall and said needle mounting portion, and so mounted around said sealing member on the medical liquid discharge port of said barrel as to slide along the outer wall of said medical liquid discharge port; a cap member mounted around said tip member; a closing member made integral with said cap member and inserted into the medical liquid passage of said tip member and the through-hole of said sealing member for closing said through-hole; and a holding member for mounting and fixing said tip member on the medical liquid discharge port of said barrel, wherein said tip member is mounted liquid-tightly on the medical liquid discharge port by mounting said holding member around said tip member and sliding downward along the skirt of said tip member to bring said engagement pawl of said tip member into engagement with said medical liquid discharge port of said syringe.

2. A pre-filled syringe as set forth in claim 1, wherein said sealing member is a rubber plug having an annular rib on said top wall.

3. A pre-filled syringe as set forth in claim 1 or claim 2, wherein said tip member is provided at the skirt thereof with an axial slit and at the outer wall of a lower end portion thereof with retaining means for engaging with said holding member.

4. A pre-filled syringe as set forth in any of claims 1 and 3, wherein said needle mounting portion includes an inner side tip and outer side female joint means which are concentrically protruded on the outer side of said top wall of said tip member.

5. A pre-filled syringe as set forth in any of claims 1 to 4, wherein said needle mounting portion is positioned eccentric from the axis of said tip member.

6. A pre-filled syringe as set forth in any of claims 1 to 5, wherein said holding member is provided at a lower end inner wall thereof with a skirt having an engagement pawl for engaging with the retaining means of said tip member, and a top wall having a hole.

7. A pre-filled syringe as set forth in any of claims 1 to 6, wherein said cap member includes concentric inner and outer caps which are mounted around the tip of said needle mounting portion and said female joint means, respectively.

8. A pre-filled syringe as set forth in claim 7, wherein said tip member is mounted liquid-tightly on the medical liquid discharge port by sliding said holding member which is temporarily assembled with the skirt upper end portion of the outer cap of said cap member downward along the outer cap and the skirt of said tip member to bring the engagement pawl of said tip member into engagement with the medical liquid discharge port of said barrel.

9. A pre-filled syringe as set forth in claim 7, wherein said outer cap is provided with a flange at a skirt lower end portion and said flange removably held between the top wall of said holding member and the top wall of said tip member.

10. A pre-filled syringe as set forth in claim 9, wherein said flange is provided with a fragile portion and said flange is broken at the fragile portion when said cap member is removed.

11. A pre-filled syringe as set forth in claim 9, wherein said flange is formed thin and said flange is transformed and comes off between the top wall of said holding member and the top wall of said tip member when said cap member is removed.

12. A pre-filled syringe as set forth in claim 11, wherein said flange is provided with a fanwise slit.

13. A pre-filled syringe as set forth in claim 7, wherein said outer cap is covered with a cylindrical cover cap which connects with the top wall of said holding member through the fragile portion, and said cylindrical cover cap can be broken from the top wall of said holding member.

14. A pre-filled syringe as set forth in claim 12, wherein said cap member is removed with said cylindrical cover cap.

* * * * *

UNITED STATES PATENT AND TRADEMARK OFFICE
CERTIFICATE OF CORRECTION

PATENT NO. : 7,041,087 B2
APPLICATION NO. : 10/240002
DATED : May 9, 2006
INVENTOR(S) : Henderson et al.

It is certified that error appears in the above-identified patent and that said Letters Patent is hereby corrected as shown below:

Col. 9 lines 30-Thur Col. 10 line 55
Delete claims 1-14 and replace therefore the following replacement claims 1-14.

1. A pre-filled syringe comprising:
    a barrel made of glass and having at a distal end thereof a medical liquid discharge port;
    a sealing member fitted in the medical liquid discharge port of the barrel and having a through-hole in the axial direction;
    a tip member comprising a skirt having an engagement pawl on a lower end inner wall thereof, a top wall, a needle mounting portion, a medical liquid deriving portion and a medical liquid passage, wherein the medical liquid passage extends through the medical liquid deriving portion, the top wall and the needle mounting portion, and wherein the tip member is mounted around the sealing member on the medical liquid discharge port of the barrel as to slide along the outer wall of the medical liquid discharge port;
    a cap member mounted around the tip member;
    a closing member integrated with the cap member and inserted into the medical liquid passage of the tip member and the through-hole of the sealing member for closing the through-hole; and
    a holding member sized and configured for mounting and fixing the tip member on the medical liquid discharge port of the barrel, wherein the tip member is mounted liquid-tightly on the medical liquid discharge port by mounting the holding member around the tip member and sliding the holding member downward along the skirt of the tip member to bring the engagement pawl of the tip member into engagement with the medical liquid discharge port of the syringe.

2. The pre-filled syringe according to claim 1, wherein the sealing member is a rubber plug having an annular rib on the top wall.

3. The pre-filled syringe according to claim 1, wherein the skirt of the tip member has one or more axial slits and retaining means at a lower end outer wall portion thereof for engaging with the holding member.

4. The pre-filled syringe according to claim 1, wherein the needle mounting portion comprises an inner side tip and outer side female joint means which concentrically protrude on the outer side of the top wall of the tip member.

5. The pre-filled syringe according to claim 1, wherein the needle mounting portion is positioned eccentric from the axis of the tip member.

UNITED STATES PATENT AND TRADEMARK OFFICE
CERTIFICATE OF CORRECTION

PATENT NO. : 7,041,087 B2
APPLICATION NO. : 10/240002
DATED : May 9, 2006
INVENTOR(S) : Henderson et al.

It is certified that error appears in the above-identified patent and that said Letters Patent is hereby corrected as shown below:

6. The pre-filled syringe according to claim 3, wherein the holding member is provided at a lower end inner wall portion thereof with a skirt having an engagement pawl sized and configured for engaging with the retaining means of the tip member.

7. The pre-filled syringe according to claim 4, wherein the cap member comprises concentric inner and outer caps, wherein the inner cap is mounted around the tip of the needle mounting portion and the outer cap is mounted around the female joint means.

8. The pre-filled syringe according to claim 7, wherein the tip member is sized and configured to be mounted liquid-tightly on the medical liquid discharge port by sliding the holding member, which is temporarily assembled with the skirt upper end portion of the outer cap of the cap member, downward along the outer cap and the skirt of the tip member to bring the engagement pawl of the tip member into engagement with the medical liquid discharge port of the barrel.

9. The pre-filled syringe according to claim 7, wherein the outer cap is provided with a flange at a skirt lower end portion thereof, wherein the flange is removably held between the top wall of the holding member and the top wall of the tip member.

10. The pre-filled syringe according to claim 9, wherein the flange is provided with a fragile portion, wherein the flange is sized and configured so that the fragile portion is broken when the cap member is removed.

11. The pre-filled syringe according to claim 9, wherein the flange is thin and adapted for breaking off between the top wall of the holding member and the top wall of the tip member when the cap member is removed.

12. The pre-filled syringe according to claim 11, wherein the flange is provided with at least one slit.

13. The pre-filled syringe according to claim 7, wherein the outer cap is covered with a cylindrical cover cap which connects with the top wall of the holding member through the fragile portion, and the cylindrical cover cap is adapted to be broken from the top wall of the holding member.

UNITED STATES PATENT AND TRADEMARK OFFICE
CERTIFICATE OF CORRECTION

PATENT NO. : 7,041,087 B2
APPLICATION NO. : 10/240002
DATED : May 9, 2006
INVENTOR(S) : Henderson et al.

It is certified that error appears in the above-identified patent and that said Letters Patent is hereby corrected as shown below:

14. The pre-filled syringe according to claim 12, wherein the cap member is removable with the cylindrical cover cap.

Signed and Sealed this

Twenty-first Day of November, 2006

JON W. DUDAS
*Director of the United States Patent and Trademark Office*